US010894758B2

(12) United States Patent
Savo et al.

(10) Patent No.: US 10,894,758 B2
(45) Date of Patent: Jan. 19, 2021

(54) METHOD OF CATALYSIS FOR THE PRODUCTION OF BISPHENOL A

(71) Applicants: DDP SPECIALTY ELECTRONIC MATERIALS US, INC., Collegeville, PA (US); DDP SPECIALTY ELECTRONIC MATERIALS US 8, LLC, Collegeville, PA (US)

(72) Inventors: Andrew M. Savo, Cherry Hill, NJ (US); Mark Vandersall, Jamison, PA (US); Klaus-Dieter Topp, Kronberg (DE); Liu Yang, Shanghai (CN)

(73) Assignees: DDP SPECIALTY ELECTRONIC MATERIALS US, INC., Collegeville, PA (US); DDP SPECIALTY ELECTRONS MATERIALS US 8, LLC, Collegeville, PA (US)

( * ) Notice: Subject to any disclaimer, the term of this patent is extended or adjusted under 35 U.S.C. 154(b) by 0 days.

(21) Appl. No.: 16/759,124

(22) PCT Filed: Oct. 24, 2018

(86) PCT No.: PCT/US2018/057385

§ 371 (c)(1),
(2) Date: Apr. 24, 2020

(87) PCT Pub. No.: WO2019/094198

PCT Pub. Date: May 16, 2019

(65) Prior Publication Data

US 2020/0339493 A1 Oct. 29, 2020

Related U.S. Application Data

(60) Provisional application No. 62/584,218, filed on Nov. 10, 2017.

(51) Int. Cl.

| | |
|---|---|
| ***C07C 37/20*** | (2006.01) |
| ***C07C 39/16*** | (2006.01) |
| ***B01J 31/08*** | (2006.01) |
| ***B01J 31/10*** | (2006.01) |
| ***B01J 35/02*** | (2006.01) |
| ***B01J 31/06*** | (2006.01) |

(52) U.S. Cl.

CPC ............... *C07C 37/20* (2013.01); *B01J 31/06* (2013.01); *B01J 31/08* (2013.01); *B01J 31/10* (2013.01); *B01J 35/026* (2013.01); *B01J 2231/347* (2013.01); *B01J 2231/4288* (2013.01); *B01J 2531/002* (2013.01)

(58) Field of Classification Search

CPC ............ C07C 37/20; B01J 31/08; B01J 31/10

See application file for complete search history.

(56) References Cited

FOREIGN PATENT DOCUMENTS

WO WO-2017013605 A1 * 1/2017 ............. B01J 31/10

* cited by examiner

*Primary Examiner* — Medhanit W Bahta

(74) *Attorney, Agent, or Firm* — Carl P. Hemenway; Kenneth Crimaldi

(57) ABSTRACT

Provided is a process for producing 2,2-bis(4-hydroxyphenyl)propane, comprising condensing phenol with acetone in the presence of an acid catalyst;

wherein the acid catalyst comprises a collection of sulfonated polymeric beads, wherein the sulfonated polymeric beads comprise (i) 75 to 99% by weight, based on the weight of the bead, polymerized units of monofunctional vinyl monomer, and (ii) 1 to 25% by weight, based on the weight of the bead, polymerized units of multifunctional vinyl monomer;

wherein 90% or more of the beads by volume are uniform beads.

4 Claims, No Drawings

METHOD OF CATALYSIS FOR THE PRODUCTION OF BISPHENOL A

A useful method of producing polymeric beads is suspension polymerization, which is a process in which monomer droplets are suspended in an aqueous medium and then the monomer in the droplets is polymerized to form polymeric beads. When a mixture of monomers is present in the monomer droplet, it is known that the monomers usually react at different rates, thus forming an inhomogeneous polymeric bead. For example, it is contemplated that one or more regions within the droplet may form copolymer that has a proportion of polymerized units of the more-reactive monomer that is higher than the average proportion of the more-reactive monomer that is present in the mixture of monomers in the whole droplet. It is contemplated that such regions that are rich in polymerized units of the more-reactive monomer would be especially likely to form early in the polymerization process. It is further contemplated that, later in the polymerization process, regions that are relatively poor in polymerized units of the more-reactive monomer would form. Thus it is contemplated that the resulting polymeric bead would be heterogeneous, with some polymer segments within the bead having different concentrations of polymerized units of the more-reactive monomer from other polymer segments. It is anticipated that this heterogeneity will be detrimental to some of the performance properties of the polymeric bead.

It is desired to provide a process for making polymeric beads that involves polymerization of a mixture of monomers that yields polymeric beads in which the distribution of polymerized units of each monomer is relatively uniform. More generally, it is further desired to provide a process by which the extent and nature of the heterogeneity can be controlled, rather than relying solely on the relative reactivities of the monomers to create uncontrolled heterogeneity. It is also desired to provide a process in which the mass transfer of monomer being fed during polymerization into the monomer droplets, where polymerization is taking place, proceeds efficiently or consistently or both, where "consistently" means that the mass transfer proceeds unusually closely to identically from one from one batch (i.e., one polymerization process) to another.

In many cases, after polymerization is complete, polymeric beads are functionalized. That is, the polymeric beads are subjected to one or more chemical reactions to attach ionic functional groups, which may be anionic groups or cationic groups, to the polymeric beads.

An important characteristic of polymeric beads is the mechanical strength. Mechanical strength may be assessed on the polymeric beads immediately after polymerization or may be assessed on functionalized beads. The mechanical strength of a bead may be measured directly, for example by measuring the force necessary to crush the bead. A higher crush strength is desirable, especially for functionalized beads. Also, the mechanical strength may be measured on polymeric beads functionalized with either anionic or cationic groups by exposing the beads to alternating solutions containing different types of ions. Exposure to these alternating solutions causes osmotic stresses that cause some polymeric beads to break. It is desirable that as few functionalized beads as possible break from osmotic stress.

U.S. Pat. No. 3,792,029 describes a process of suspension polymerization in which, during suspension polymerization of a monomer mixture, an emulsion containing the more-reactive monomer is added to the suspension while polymerization is occurring. It is desired to provide a process in which neat monomer is added to a suspension polymerization process. It is also desired to provide polymeric beads having one or more of the following benefits: relatively homogeneous distribution of polymerized units of each monomer, high crush strength, consistent and/or efficient mass transfer of feed monomer to monomer droplets, and/or high resistance to osmotic stress.

Additionally, in the process described by U.S. Pat. No. 3,792,029, the emulsion added to the suspension during polymerization contains a mixture of the more-reactive monomer and the less-reactive monomer. In the mixture added to the suspension described by U.S. Pat. No. 3,792,029, there is considerably more (by weight) of the less-reactive monomer than more-reactive monomer. It is considered that the process described by U.S. Pat. No. 3,792,029 can lead to one or more of the following undesirable effects: the process may cause an increase in the bead size, which places undesirable stress on the polymer network; and/or the process may lead to the formation of inhomogeneity in the structure of the bead, for example by forming interpenetrating polymer networks. It is desired to provide a process in which the monomer added to the suspension during polymerization is 50% or more by weight of the more-reactive monomer. It is also desired to provide a process that avoids the undesirable effects of the process of U.S. Pat. No. 3,792,029.

The following is a statement of the invention.

A first aspect of the present invention is a process of making a collection of polymeric beads, wherein the beads comprise (i) 75 to 99% by weight, based on the weight of the bead, polymerized units of monofunctional vinyl monomer, and (ii) 1 to 25% by weight, based on the weight of the bead, polymerized units of multifunctional vinyl monomer;

wherein the process comprises (a) providing an aqueous suspension of monomer droplets comprising initiator, monofunctional vinyl monomer, and multifunctional vinyl monomer;

(b) initiating polymerization of the monomer in the monomer droplets;

(c) while the polymerization of the monomer in the monomer droplets is occurring, adding a monomer feed solution to the suspension wherein the adding begins at a time when the extent of polymerization of monomer in the monomer droplets (EXTSTART) is 0% to 50%, and wherein the adding ends at a time after EXTSTART when the extent of polymerization of monomer in the monomer droplets (EXTSTOP) is 5% to 100%;

wherein the feed solution comprises monomer in an amount, by weight based on the weight of the feed solution, of 90% to 100%;

wherein the feed solution comprises multifunctional vinyl monomer in an amount, by weight based on the weight of the feed solution, of 50% to 100%.

A second aspect of the present invention is a collection of polymeric beads, wherein the beads comprise (i) 75 to 99% by weight, based on the weight of the bead, polymerized units of monofunctional vinyl monomer, and (ii) 1 to 25% by weight, based on the weight of the bead, polymerized units of multifunctional vinyl monomer;

wherein, within each bead, the average concentration of moles of polymerized units of multifunctional vinyl monomer per cubic micrometer is MVAV;

wherein, within each bead, T1000 is a sequence of 1,000 unique connected polymerized monomer units;

wherein, within each T1000, MVSEQ is the weight percent polymerized units of multifunctional vinyl monomer, based on the weight of T1000;

wherein MVRATIO=MVSEQ/MVAV;

and wherein 90% or more of the beads by volume are uniform beads, wherein a uniform bead is a bead in which 90% or more of all T1000 sequences has MVRATIO of 1.5 or less.

A third aspect of the present invention is a process for treating water, wherein the water comprises dissolved ions that comprise an undesired cation, wherein the process comprises (a) providing a collection of functionalized polymeric beads that comprise (i) 75 to 99% by weight, based on the weight of the bead, polymerized units of monofunctional vinyl monomer, and (ii) 1 to 25% by weight, based on the weight of the bead, polymerized units of multifunctional vinyl monomer;

(iii) functional groups that are bonded to the polymeric beads and that have charge opposite to the charge of the undesired ion, and (iv) ions that are not bonded to the polymeric beads and that have charge the same as the undesired ion;

wherein, within each bead, the average concentration of moles of polymerized units of multifunctional vinyl monomer per cubic micrometer is MVAV;

wherein, within each bead, T1000 is a sequence of 1,000 unique connected polymerized monomer units;

wherein, within each T1000, MVSEQ is the weight percent polymerized units of multifunctional vinyl monomer, based on the weight of T1000;

wherein MVRATIO=MVSEQ/MVAV;

and wherein 90% or more of the beads by volume are uniform beads, wherein a uniform bead is a bead in which 90% or more of all T1000 sequences has MVRATIO of 1.5 or less;

(b) then passing the water through a bed of the collection of polymeric beads to exchange the undesired ion for the ions (iv), (c) then passing a regeneration solution comprising dissolved ions (v) of the same species as ions (iv) through the bed of the collection of polymeric beads to exchange ions (v) for the undesired ions.

A fourth aspect of the present invention is a process for producing 2,2-bis(4-hydroxyphenyl)propane, comprising condensing phenol with acetone in the presence of an acid catalyst to produce dihydric phenol 2,2-bis(4-hydroxyphenyl) propane;

wherein the acid catalyst comprises a collection of sulfonated polymeric beads, wherein the sulfonated polymeric beads comprise (i) 75 to 99% by weight, based on the weight of the bead, polymerized units of monofunctional vinyl monomer, and (ii) 1 to 25% by weight, based on the weight of the bead, polymerized units of multifunctional vinyl monomer;

wherein, within each bead, the average concentration of moles of polymerized units of multifunctional vinyl monomer per cubic micrometer is MVAV;

wherein, within each bead, T1000 is a sequence of 1,000 unique connected polymerized monomer units;

wherein, within each T1000, MVSEQ is the weight percent polymerized units of multifunctional vinyl monomer, based on the weight of T1000;

wherein MVRATIO=MVSEQ/MVAV;

and wherein 90% or more of the beads by volume are uniform beads, wherein a uniform bead is a bead in which 90% or more of all T1000 sequences has MVRATIO of 1.5 or less.

The following is a detailed description of the invention.

As used herein, the following terms have the designated definitions, unless the context clearly indicates otherwise.

A "polymer," as used herein is a relatively large molecule made up of the reaction products of smaller chemical repeat units. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof.

Molecules that can react with each other to form the repeat units of a polymer are known herein as "monomers." The repeat units so formed are known herein as "polymerized units" of the monomer.

Vinyl monomers have the structure

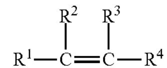

where each of $R^1$, $R^2$, $R^3$, and $R^4$ is, independently, a hydrogen, a halogen, an aliphatic group (such as, for example, an alkyl group), a substituted aliphatic group, an aryl group, a substituted aryl group, another substituted or unsubstituted organic group, or any combination thereof. Vinyl monomers are capable of free radical polymerization to form polymers. Some vinyl monomers have one or more polymerizable carbon-carbon double bonds incorporated into one or more of $R^1$, $R^2$, $R^3$, and $R^4$; such vinyl monomers are known herein as multifunctional vinyl monomers. Vinyl monomers with exactly one polymerizable carbon-carbon double bond are known herein as monofunctional vinyl monomers.

Styrenic monomers are vinyl monomers in which each of $R^1$ and $R^2$ is hydrogen, $R^3$ is hydrogen or alkyl, and —$R^4$ has the structure

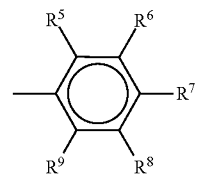

where each of $R^5$, $R^6$, $R^7$, $R^8$, and $R^9$ is, independently, a hydrogen, a halogen, an aliphatic group (such as, for example, an alkyl group or a vinyl group), a substituted aliphatic group, an aryl group, a substituted aryl group, another substituted or unsubstituted organic group, or any combination thereof.

A reaction among monomers to form one or more polymers is referred to herein as a polymerization process.

As used herein, an initiator is a molecule that is stable at ambient conditions but that is capable under certain conditions of producing one or more fragments that bears a free radical, and that fragment is capable of interacting with a monomer to start a free radical polymerization process. The conditions that cause production of a fragment bearing a free radical include, for example, elevated temperature, participation in an oxidation-reduction reaction, exposure to ultraviolet and/or ionizing radiation, or a combination thereof.

As used herein the phrase "total monomer" refers to all the monomers used in making a polymer, including monomers that are present when initiation of polymerization begins and all of those that may be added during the polymerization processes.

A polymer is said herein to contain polymerized units of the monomers used in making the polymer, even if some or all of those polymerized units are, after polymerization, altered by the addition of one or more functional groups. For example, a copolymer made from styrene and DVB in a weight ratio of styrene:DVB of 90:10 is said to have 90% by weight polymerized units of styrene. If that copolymer were to be then altered by reaction with sulfuric acid to replace some of the hydrogen atoms on aromatic rings with sulfonic acid groups, the resulting functionalized polymer would still be said to have 90% by weight polymerized units of styrene.

As used herein, an inhibitor is a molecule that reacts with a vinyl monomer radical or with the radical on a growing vinyl polymer chain to form a new radical that does not participate in vinyl polymerization.

Macroporous polymeric beads have a porous structure with average pore diameter of 20 nm or larger. Pore diameter is measured using the Brunauer-Emmett-Teller (BET) method using nitrogen gas. Macroporous polymeric beads are normally made by incorporating a porogen into monomer droplets. The porogen is soluble in the monomer, but the polymer does not dissolve in the porogen, so that, as the polymer forms, phase-separated domains of porogen remain. After polymerization, the porogen is removed by evaporation or by washing with solvent. The porous structure of the polymeric bead is the empty space left when the porogen is removed from its phase-separated domains.

Gel type polymeric beads are made without the use of porogen. The pores in gel type polymeric beads are the free volumes between the atoms in the entangled, possibly crosslinked polymer chains of the polymeric bead. The pores in gel type polymeric beads are smaller than 20 nm. In some cases, the pores in gel type resins are too small to be detected using the BET method.

Two ions or ionic groups are said herein to have the "same" charge if both are anionic or if both are cationic, regardless of the magnitude of the charge. For example, a sulfonate group (i.e., $—SO_3^-$) is said to have the same charge as a carbonate ion (i.e., $CO_3^{2-}$). Similarly, two ions or ionic groups are said herein to have "opposite" charge if one is anionic and the other cationic, regardless of the magnitude of the charge. Carboxylic acid groups are considered to comprise a carboxylate anion and a hydrogen cation, and sulfonic acid groups are considered to comprise a sulfonate anion and a hydrogen cation).

As used herein, ion exchange is a process in which a solution comes into contact with an ion exchange resin. Prior to the contact with the solution, the ion exchange resin has functional groups of a certain charge, and has ions of the opposite charge associated with the functional groups. When the solution comes in contact with the ion exchange resin, some ions in solution become attached to the ion exchange resin by exchanging places with ions of the same charge that had been associated with the functional groups on the ion exchange resin.

A compound is said herein to be water-soluble if 5 grams or more of the compound forms a stable solution in 100 ml of water at 25° C. In the case of some water-soluble polymers, the water may need to be heated above 25° C. in order to make the polymer dissolve, but after cooling to 25° C., the solution is stable when held at 25° C.

A suspension is a composition that has particles of one substance distributed through a liquid medium. The distributed particles may be liquid or solid; distributed liquid particles are called droplets. The medium is "aqueous" if the medium contains 90% or more water by weight, based on the weight of the medium. A suspension may or may not be stable. That is, the distributed particles may or may not have a tendency to settle to the bottom of the container or to float to the top of the container, and mechanical agitation may or may not be required to keep the particles distributed in the medium.

A polymeric bead is a particle that contains 90% or more by weight, based on the weight of the particle, organic polymer. A polymeric bead is spherical or nearly spherical. A polymeric bead is characterized by its radius. If the bead is not spherical, the radius of the bead is taken herein to be the radius of a "reference sphere," which is the imaginary sphere that has the same volume as the bead. Whether a particle is spherical or not is assessed by the "sphericity," represented by the Greek letter T. For a particle having volume VP, and principal axes of length a (long), b (medium) and c (short), the sphericity is $$\Psi = \left(\frac{bc}{a^2}\right)^{1/3}$$

The unit of volume "cubic micrometer" (abbreviated $\mu m^3$) as used herein refers to the volume of a cube that has edge length of 1 micrometer.

As used herein, "ambient temperature" is synonymous with "room temperature" and is approximately 23° C.

A collection of particles has harmonic mean diameter (HMD) defined as follows:

$$HMD = \frac{n}{\sum_{i=1}^{n} (1/d_i)}$$

where n is the number of particles, and di is the diameter of the $i^{th}$ particle.

Ratios are characterized herein as follows. For example, if a ratio is said to be 5:1 or higher, it is meant that the ratio may be 5:1 or 6:1 or 100:1 but may not be 4:1. To state this characterization in a general way, if a ratio is said to be X:1 or higher, then the ratio is Y:1, where Y is greater than or equal to X. Similarly, for example, if a ratio is said to be 2:1 or lower, it is meant that the ratio may be 2:1 or 1:1 or 0.001:1 but may not be 3:1. To state this characterization in a general way, if a ratio is said to be Z:1 or lower, then the ratio is W:1, where W is less than or equal to Z.

The process of the present invention involves monomer droplets that contain vinyl monomer and initiator. The following is a description of the monomer droplets as they exist prior to initiation of polymerization.

Preferably, the amount of monomer in the monomer droplets is, by weight based on the weight of the droplets, 80% or more; more preferably 90% or more; more preferably 95% or more.

Preferred vinyl monomers are styrenic monomers, acrylic monomers, and mixtures thereof. Preferably, all the monomers used are selected from styrenic monomers, acrylic monomers, and mixtures thereof. More preferably, all the monomers used are selected from styrenic monomers. The vinyl monomer includes one or more monofunctional vinyl monomers. Preferred monofunctional vinyl monomers are acrylic and styrenic monofunctional monomers; more preferred are monofunctional styrenic monomers; more preferred is styrene. The vinyl monomer also includes one or more multifunctional vinyl monomers. Preferred multifunctional vinyl monomers are multifunctional styrenic monomers; more preferred is divinyl benzene. Preferably, the amount of vinyl chloride is, by weight based on the total weight of all monomers, 0 to 0.1%, more preferably 0 to 0.01%; more preferably 0%.

Preferably, the amount of styrenic monomer in the droplets prior to initiation of polymerization, by weight based on the weight of all monomers in the droplets, is 50% or higher; more preferably 75% or higher; more preferably 88% or higher; more preferably 94% or higher; more preferably 97% or higher; more preferably 100%.

Preferably, the amount of monofunctional vinyl monomer in the droplets prior to initiation of polymerization is, by weight based on the weight of all monomers in the droplets, 75% or more; more preferably 80% or more; more preferably 85% or more: more preferably 90% or more; more preferably 94% or more. Preferably, the amount of monofunctional vinyl monomer in the droplets is, by weight based on the weight of all monomers in the droplets, 99.9% or less; more preferably 99% or less; more preferably 98.5% or less.

Preferably, the amount of multifunctional vinyl monomer in the droplets prior to initiation of polymerization is, by weight based on the weight of all monomers in the droplets, 0.1% or more; more preferably 1% or more; more preferably 1.5% or more. Preferably, the amount of multifunctional vinyl monomer in the droplets is, by weight based on the weight of all monomers in the droplets, less than 25%; more preferably 20% or less; more preferably 15% or less; more preferably 10% or less; more preferably 6% or less.

It is useful to characterize the amount ("MFMPRIOR") of multifunctional vinyl monomer in the droplets prior to initiation of polymerization as a weight percentage of the total monomer. Preferably MFMPRIOR is 0.1% or more; more preferably 0.5% or more; more preferably 1% or more; more preferably 1.5% or more; more preferably 2% or more. Preferably MFMPRIOR is 10% or less; more preferably 8% or less; more preferably 6% or less.

It is also useful to characterize the ratio

MFMRATIO=100*MFMPRIOR/MFMTOTAL where MFMTOTAL is the total weight percentage of multifunctional monomer used in the entire polymerization process, including multifunctional monomer present prior to initiation and multifunctional monomer added after initiation. Preferably WMRATIO is 10% or more; more preferably 20% or more; more preferably 30% or more. Preferably WMRATIO is 80% or less; more preferably 70% or less; more preferably 60% or less.

The process of the present invention involves a suspension of the monomer droplets in an aqueous medium. Preferably, the total amount of monomer, by weight based on the total weight of the suspension, is 5% or more; more preferably 10% or more; more preferably 15% or more. Preferably, the total amount of monomer, by weight based on the total weight of the suspension, is 55% or less; more preferably 35% or less; more preferably 30% or less.

The monomer droplets contain one or more initiator. Preferred initiators have solubility in 100 mL of water at 25° C. of 1 gram or less; more preferably 0.5 gram or less; more preferably 0.2 gram or less; more preferably 0.1 gram or less. Preferred are organic peroxide and hydroperoxide initiators; more preferred are peroxide initiators; more preferred are benzoyl peroxide and derivatives thereof; more preferred is benzoyl peroxide. Preferably, the weight ratio of initiator to total monomer is 0.0002:1 or higher; more preferably 0.0005:1 or higher; more preferably 0.001:1 or higher; more preferably 0.002:1 or higher. Preferably, the weight ratio of initiator to total monomer is 0.02:1 or lower; more preferably 0.01:1 or lower; more preferably 0.007:1 or lower.

The monomer droplets optionally contain one or more porogen. Preferably, little or no porogen is present. That is, preferably either porogen is absent or else, if present, the amount of porogen is, by weight based on the weight of monomer droplets, 1% or less; more preferably 0.1% or less. More preferably, no porogen is present in the monomer droplets.

Monomers, as normally supplied by manufacturers, contain relatively small amounts of inhibitors, to prevent accidental polymerization during storage. Common inhibitors are quinones (for example, 1,4-benzoquinone) and hindered phenols (for example, 4-tert-butylpyrocatechol, also called 4-t-butylcatechol).

Preferably, prior to the initiation of polymerization, the monomer droplets either contain no polymer of any kind or else contain small amounts of polymer of any kind. That is, if any polymer is present in the monomer droplets, the total amount of polymer is preferably, by weight based on the weight of the monomer droplets, 0.1% or less.

The aqueous medium preferably contains one or more water-soluble polymer. Water-soluble polymers are considered to stabilize the monomer droplets against coalescence. Suitable water-soluble polymers may be any of a wide variety of polymer types. Preferred water-soluble polymers are water-soluble polyvinyl alcohol polymers, water-soluble derivatives of cellulose, quaternary ammonium polymers, gelatin, and mixtures thereof. More preferred water-soluble polymers are water-soluble polyvinyl alcohol polymers, water-soluble derivatives of cellulose, and mixtures thereof. Among quaternary ammonium polymers, preferred are polymers of diallyl dimethylammonium chloride (DADMAC). Among water-soluble derivatives of cellulose, preferred are carboxymethyl methylcelluloses. Among polyvinyl alcohol polymers, preferred are those with degree of hydrolysis of 80% to 90%. Preferably the aqueous medium contains one or more water-soluble polyvinyl alcohol polymers and one or more water-soluble derivatives of cellulose.

When one or more water-soluble polymers are used, preferably the total amount of water-soluble polymers is, by weight based on the weight of the aqueous medium, 0.02% or higher; more preferably 0.05% or higher; more preferably 0.1% or higher. When one or more water-soluble polymers are used, preferably the total amount of water-soluble polymers is, by weight based on the weight of the water, 2% or less; more preferably 1% or less; more preferably 0.5% or less.

Also suitable are other methods of stabilizing monomer droplets, which may be used instead of one or more water-soluble polymers or in addition to one or more water-soluble polymers. For example, solid particles that are smaller than the monomer droplets may reside at the surface of the droplets and stabilize the droplets. One example of such solid particles is colloidal silica particles.

The aqueous suspension of monomer droplets optionally contains one or more suspension aids. Suspension aids are considered to stabilize the monomer droplets. Suspension aids may be introduced by adding them to the aqueous phase or by adding them to the monomer droplets or by a combination thereof. Regardless of how the suspension aid is introduced, a preferred amount of suspension aid, by weight based on the weight of the monomer droplets, 0.001% to 0.1%. A preferred suspension aid is 4-vinylphenyl boronic acid.

The nature of the step that initiates polymerization depends in part on the nature of the initiator that is used. For example, when a thermal initiator is used, initiation conditions involve establishing a temperature above 25° C. that is high enough for a significant fraction of the initiator molecules to decompose to form free radicals. For another example, if a photoinitiator is used, initiation conditions involve exposing the initiator to radiation of sufficiently low wavelength and of sufficiently high intensity for a significant fraction of the initiator molecules to decompose to form free radicals. For another example, when the initiator is a redox initiator, initiation conditions involve the presence of sufficiently high concentration of both the oxidant and the reductant such that a significant number of free radicals are produced. Preferably, a thermal initiator is used. Preferably, initiation conditions involve temperature of 55° C. or higher; more preferably 70° C. or higher. That is, preferably the suspension is provided at a temperature below 40° C., and the initiator that is present does not produce significant number of free radicals at that temperature. Then, preferably, step (b) involves raising the temperature to initiation conditions.

After step (b), while polymerization is taking place, at any specific moment, the extent of the free radical polymerization in the vessel that contains the suspension may be characterized as follows.

$$\text{Extent}=100*\text{PM}/\text{TM}$$

where PM is the mass of polymer formed by the free radical polymerization process, and TM is the total mass of monomer that has been added to the vessel up to that moment (including both the initial monomer droplets and monomer added during the course of the polymerization).

Prior to the beginning of the polymerization process, droplets are present in the suspension, and the droplets contain vinyl monomer and initiator. Preferably the droplets are distributed throughout the aqueous medium. Preferably the composition of the aqueous medium contains water in the amount, by weight based on the weight of the aqueous medium, of 90% or more; more preferably 95% or more; more preferably 97% or more. Compounds dissolved in the water are considered to be part of the continuous liquid medium. Preferably, the volume average particle size of the droplets is 50 μm to 1,500 μm.

In the process of the present invention, once the polymerization in the monomer droplets has begun, a feed solution is added to the suspension. The action of adding monomer to the suspension after polymerization has begun is known herein as "gradual addition," or GA. The feed solution may be added at any rate. The rate of adding the feed solution may be steady or may be faster at some times than other times. Adding the feed solution may be accomplished in a single continuous addition (which may be performed quickly or slowly), or adding the feed solution may be interrupted one or more times.

Adding the feed solution is begun when the extent of reaction is at a point herein labeled "EXTSTART." EXTSTART is between 0% and 50%, inclusive. Preferably, EXTSTART is 40% or lower; more preferably 30% or lower; more preferably 20% or lower; more preferably 10% or lower.

The extent of reaction "EXTSTOP" is the extent of reaction at which the last of the feed solution is added to the suspension. No feed solution is added to the suspension after EXTSTOP. EXTSTOP is 5% to 100%. Preferably EXTSTOP is 85% or less. Preferably the quantity $$\text{EXTDIFF}=\text{EXTSTOP}-\text{EXTSTART}$$

is 5% or higher; more preferably 20% or higher; more preferably 50% or higher; more preferably 60% or higher.

Preferably, the feed solution contains total vinyl monomer of all types in an amount, by weight based on the weight of the feed solution, 75% or more; more preferably 85% or more; more preferably 95% or more; more preferably 99% or more.

The amount of multifunctional monomer in the feed solution is preferably, by weight based on the weight of the feed solution, 30% or more; preferably 40% or more; more preferably 45% or more; more preferably 50% or more; more preferably 55% or more; more preferably 60% or more. When the multifunctional monomer is divinylbenzene (DVB), it is suitable to use an industrial grade of DVB, which is a mixture that contains approximately 63% chemically pure DVB by weight and approximately 37% ethylvinylbenzene (EVB) by weight, with other impurities totaling less than 1% by weight. When it is stated here that a composition contains a certain amount of DVB, it is assumed that the composition contains, in addition to that stated amount of DVB, EVB at a weight ratio of EVB:DVB of approximately 37:63. When such an industrial grade of DVB is used, preferably the amount of the industrial grade of DVB in the feed solution, by weight based on the weight of the feed solution, is 50% or more; more preferably 60% or more; more preferably 70% or more; more preferably 80% or more; more preferably 90% or more; more preferably 95% or more.

Preferably, the feed solution either contains no initiator or else contains initiator in an amount, in parts per million by weight, of 100 ppm or less; more preferably 10 ppm or less; more preferably 1 ppm or less.

Preferably, the feed solution either contains no water or contains water in an amount, by weight based on the weight of the feed solution, of 20% or less; more preferably 10% or less; more preferably 3% or less; more preferably 1% or less; more preferably 0.3% or less; more preferably 0.1% or less.

Also envisioned are embodiments ("dispersion feed" embodiments) in which the feed solution is replaced by a feed composition that is a dispersion of monomer droplets in an aqueous medium. Such a dispersion may be any type of, dispersion, including, for example, suspension, emulsion, microemulsion, or nanoemulsion. Such a dispersion optionally contains one or more water-soluble polymer as described above, one or more surfactant, one or more dispersant, or a mixture thereof. Among dispersion feed embodiments, preferred are emulsions. Among emulsions, preferred are those that contain one or more anionic surfactant.

In dispersion feed embodiments, the total amount of monomer in the feed composition is, by weight based on the weight of the feed composition, 5% or more; more preferably 10% or more; more preferably 20% or more; more preferably 40% or more. In dispersion feed embodiments, the total amount of monomer in the feed composition is, by weight based on the weight of the feed composition, 60% or less; more preferably 55% or less.

In dispersion feed embodiments, it is useful to characterize the amount of multifunctional vinyl monomer as a weight percentage of the monomer content of the feed composition. In dispersion embodiments, preferably the amount of multifunctional vinyl monomer is, by weight based on the total weight of monomers in the feed composition, 50% to 100%; more preferably 75% to 100%; more preferably 90% to 100%; more preferably 95% to 100%.

In dispersion feed embodiments, the suitable and preferable conditions for feeding during polymerization (extent of reaction, etc.) are the same as those described above.

The present invention also involves a collection of polymeric beads. The collection of polymeric beads is preferably made by the method of the present invention. The polymeric beads contain polymer. Polymeric beads are particles that are solid at 25° C. and that contain polymer in the amount, by weight based on the weight of the polymeric particles, of 90% or more; more preferably 95% or more.

The polymeric beads may be macroporous beads or gel beads. Preferred are gel beads.

Preferably the polymeric beads have volume average particle diameter of 50 μm or larger; more preferably 100 μm or larger; more preferably 200 μm or larger; more preferably 400 μm or larger. Preferably the polymeric beads have volume average particle diameter of 1,500 μm or lower; more preferably 1,000 μm or lower.

Preferred polymers in the polymeric particles are the polymers formed by free radical polymerization of the preferred vinyl monomers described above. Preferably the polymer contains polymerized units of styrenic monomer in the amount, by weight based on the weight of the polymer, of 5% or more; more preferably 25% or more; more preferably 50% or more; more preferably 75% or more; more preferably 95% or more. The types of monomers preferred as polymerized units of the polymer are the same as those described above as preferred for use in the polymerization process.

Preferred polymers have polymerized units of multifunctional vinyl monomer in an amount, by weight based on the weight of the polymer, of 1% or more; more preferably 1.5% or more; more preferably 2% or more. Preferred polymers have polymerized units of multifunctional vinyl monomer in an amount, by weight based on the weight of the polymer, of 25% or less; more preferably 20% or less; more preferably 15% or less; more preferably 11% or less; more preferably 6% or less.

Preferred polymers have polymerized units of monofunctional vinyl monomer in an amount, by weight based on the weight of the polymer, of 99.7% or less; more preferably 99.5% or less; more preferably 99% or less; more preferably 98.5% or less. Preferred polymers have polymerized units of monofunctional vinyl monomer in an amount, by weight based on the weight of the polymer, of 75% or more; more preferably 80% or more; more preferably 85% or more; more preferably 90% or more; more preferably 94% or more.

The polymer in the polymeric bead has a relatively even distribution of polymerized units of multifunctional vinyl monomer. The uniformity of the distribution of polymerized units of multifunctional vinyl monomer may be characterized as follows.

MVAV=the average concentration (in moles per cubic micrometer) of polymerized units of multifunctional vinyl monomer within a single bead T1000=a sequence of 1,000 connected polymerized monomer units MVSEQ=for a specific T1000, the weight percent of polymerized units of multifunctional vinyl monomer, based on the weight of T1000

MVRATIO=MVSEQ/MVAV

In choosing a T1000, any polymerized unit may be chosen as the first unit of the sequence. Then any polymerized unit that is covalently bonded to the first polymerized unit may be chosen as the second unit in the sequence. Similarly, each unit that is chosen is covalently bonded to the previous unit in the sequence. No polymerized unit may occur twice in the T1000 sequence. When 1000 polymerized units have been chosen, the T1000 sequence is complete. Another way to describe the process of selecting a T1000 is to state that a first polymerized unit is picked, and then a path is traced along covalently bonded polymerized units until the path is 1000 units long. The path is chosen so that it does not cross itself. Each bead contains many T1000 sequences. The T1000 sequence is not physically altered or removed from the bead. The T1000 sequence is a tool for characterizing the degree of uniformity of a polymeric bead.

The bead is considered to be "uniform" if it has a relatively even distribution of polymerized units of multifunctional vinyl monomer. That is, a bead is uniform if 90% or more, by number of sequences, of all T1000 sequences in the bead has MVRATIO of 1.5 or less. Preferred beads have a higher degree of uniformity, such that 90% or more, by number of sequences, of all T1000 sequences in the beads has MVRATIO of 1.25 or less.

In the collection of beads of the present invention, most of the beads are uniform. That is, the amount of beads, by volume, that are uniform is 90% or higher; more preferably 95%% or higher; more preferably 99% or higher. More preferably, the amount of beads, by volume, in which 90% or more, by number of sequences, of all T1000 sequences has MVRATIO of 1.25 or less is 90% or higher; more preferably 95% or higher; more preferably 99% or higher.

It is useful to consider the percentage of T1000 sequences, by number of sequences, that have MVRATIO of 0.5 or less. Preferably, 35% or less, by number of sequences, of the T1000 sequences will have MVRATIO of 0.5 or less. More preferably, 25% or less, by number of sequences, of the T1000 sequences will have MVRATIO of 0.5 or less.

The polymeric beads preferably have average sphericity of 0.8 or higher; more preferably 0.85 or higher; more preferably 0.9 or higher; more preferably 0.95 or higher.

A preferred use of the polymer produced in the free radical polymerization process of the present invention is to be used in a conversion process to produce an ion exchange resin. Ion exchange resins fall into the following categories. Weak base anion exchange resins have pendant amino groups that are primary, secondary, or tertiary. Strong base anion exchange resins have pendant quaternary amino groups. Weak acid cation exchange resins have pendant carboxylic acid groups. Strong acid cation exchange resins have pendant sulfonic acid groups. When any of these pendant functional groups have been attached to a polymer bead, the bead is referred to as a "functionalized resin."

Typically, in the preparation of weak base anion exchange resins from polymeric beads such as crosslinked polystyrene beads, the beads are advantageously haloalkylated, preferably halomethylated, most preferably chloromethylated, and the ion active exchange groups subsequently attached to the haloalkylated copolymer. Typically, the haloalkylation reaction consists of swelling the crosslinked addition copolymer with haloalkylating agent, preferably bromomethylmethyl ether, chloromethylmethyl ether, or a mixture of formaldehyde and hydrochloric acid, most preferably chloro-methylmethyl ether and then reacting the copolymer and haloalkylating agent in the presence of a Friedel-Crafts catalyst such as zinc chloride, iron chloride, or aluminum chloride. Typically, a weak base anion exchange resin is prepared by reacting the haloalkylated copolymer with ammonia, a primary amine, or a secondary amine. Typically, a strong base anion exchange resin is prepared by reacting the haloalkylated copolymer with a tertiary amine.

Typically, in the preparation of strong acid cation exchange resins from polymeric beads such as crosslinked polystyrene beads, the beads are advantageously sulfonated. Generally, the bead is swollen using a suitable swelling agent and the swollen bead reacted with a sulfonating agent such as sulfuric or chlorosulfonic acid or sulfur trioxide or a mixture thereof.

A collection of functionalized polymeric beads normally contains water in addition to the polymeric beads themselves. Normally, the process that is used for making the functionalized polymeric beads involves contact between the functionalized polymeric beads and water, and the excess liquid water is removed, but a substantial amount of water remains as part of the collection of functionalized polymeric beads. It is contemplated that the water is adsorbed into the functionalized polymeric beads. The amount of water is typically 30% to 90% by weight based on the weight of the collection of functionalized polymeric beads.

It is contemplated that the polymeric beads of the present invention would be useful for a variety of purposes. Functionalized polymeric beads would be useful for many of the purposes where ion exchange resins are useful. For example, it is expected that the increased crush strength and osmotic stability of the functionalized polymeric beads of the present invention would make these beads useful in the preferred uses as water-purification resins or as catalysts. When functionalized polymeric beads of the present invention are used as catalysts, it is expected that the functionalized polymeric beads of the present invention would improve the reaction rate of the reaction being catalyzed. The uniformity of the spatial distribution of polymerized units of multifunctional vinyl monomer in the functionalized polymeric beads of the present invention is expected to have the effect that more of the sites on the beads that are accessible for catalysis will also have the optimum concentration of polymerized units of multifunctional monomer for optimum reaction rate, as compared to previously-known beads.

Preferred methods of using the polymeric beads of the present invention involve passing a liquid through a bed of the polymeric beads. That is, a collection of the polymeric beads is placed in a container that traps the polymeric beads in place, that has an inlet for a liquid to enter the container, that allows the liquid to flow through the container while making intimate contact with the polymeric beads, and that has an outlet for the liquid to exit the container.

When the intended use is water purification, the functionalized resin is employed to remove undesirable ions from the water. The resin has functional groups (herein "functional groups (iii)"). The resin is chosen so that the functional groups (iii) have charge opposite to the charge on the undesirable ion. Prior to the purification, the functional groups (iii) are associated with counterions (herein called "ions (iv)") that are not bonded to the resin. Ions (iv) have the same charge as the undesirable ions. Preferably, the proportion of the functional groups (iii), on a molar basis, that is associated with ions (iv), is 50% or more; more preferably 75% or more; more preferably 92% or more.

In a "loading" step, the water to be purified is passed through a bed of the resin, and the undesirable ions in the water load onto the functionalized polymeric bead by associating with the functional groups (iii), in exchange for the ions (iv). Eventually the resin becomes loaded at or near its capacity for retaining the undesirable ion. Then, to remove the undesirable resin, the functionalized polymeric bead undergoes a "regeneration" step in which a regeneration solution is passed through the bed of resin. The regeneration solution contains dissolved ions including ions (v) that are the same species as ions (iv). The ions (v) replace the undesirable ions on the resin, and the undesirable ions are removed along with the regeneration solution.

Preferably, the cycle of loading and regeneration is repeated. That is, a new batch of water containing the same undesirable ion is passed through the bed of resin to load the resin with the undesirable ion, and then the resin is regenerated as described above. Preferably, the process of loading and regeneration is repeated 10 or more times; more preferably 20 or more times.

Repeated cycles of loading and regeneration causes osmotic shock to the functionalized polymeric bead, because equilibrium water content (and therefore bead size) is a function of the specific counter ion. Repeated cycles can cause some or all of the polymeric beads to break. Preferably, the polymeric beads of the present invention minimize such breakage.

The above discussion envisions a single undesirable ion of a certain charge. If the water additionally contains a second undesirable ion of opposite charge to the first undesirable ion, then it is envisioned that the water could be brought into contact with a second resin that has functional groups of charge opposite to the charge on the functional groups on the first resin. The two resins may be used in sequence or may be mixed together.

For example, a polymeric bead that is functionalized with sulfonic acid groups is a strong acid cation exchange resin ("SAC"). An SAC could be used for removing unwanted sodium ions from water. At the outset, the SAC could be in hydrogen form. That is, more than half (on a molar basis) of the sulfonate groups have counter ion $H^+$. Then an aqueous solution of NaCl could be passed through the bed of the SAC, to exchange the hydrogen ions for sodium ions, so that the sodium ions are retained on the SAC, putting the resin into sodium form, in a process called "loading" the resin. Eventually, the SAC reaches or approaches the limit of its ability to retain sodium ions. Then the SAC can be regenerated, for example by passing an aqueous solution of $H_2SO_4$ through a bed of the SAC, to put the resin back into hydrogen form. Such a cycle of loading followed by regeneration puts the resin beads under osmotic pressure, because the sodium form and hydrogen form have different equilibrium water content, and the osmotic shock of repeated cycles tends to break some of the beads.

For another example, a polymeric bead that is functionalized with quaternary ammonium groups is a strong base anion exchange resin ("SBA"). An SBA could be used for removing unwanted chloride ions from water. At the outset, the SBA could be in hydroxide form. That is, more than half (on a molar basis) of the quaternary amonium groups have counter ion $OH^-$. Then an aqueous solution of NaCl could be passed through the bed of the SBA, to exchange the hydroxide ions for chloride ions, so that the chloride ions are retained on the SBA, in a process called "loading" the resin. Eventually, the SBA reaches or approaches the limit of its ability to retain chloride ions. Then the SBA can be regenerated, for example by passing an aqueous solution of NaOH through a bed of the SBA, to put the resin back into hydroxide form. Such a cycle of loading followed by regeneration puts the resin beads under osmotic pressure, because the chloride form and the hydroxide form have different equilibrium water content, and the osmotic shock of repeated cycles tends to break some of the beads.

Analogous processes of loading and regenerating may be performed by these or other resins for removing these or other ions. Weak acid cation exchange resins or strong acid cation exchange resins may be used for removing either monovalent or multivalent cations. Weak base anion exchange resins or strong base cation exchange resins may be used for removing unwanted monovalent and/or multivalent anions. Any of these processes that involve loading and regenerating cycles create osmotic stress on the resin beads.

When the intended use is water purification, the resistance to crushing and the resistance to osmotic shock make the resins of the present invention advantageous. Because the beads have less tendency to break, a given collection of beads will have a longer lifetime in use before the beads need to be replaced. Also, when beads break, the fragments fill up the interstitial spaces between the beads, which impedes the flow of water through the bed of beads, which causes increased pressure drop in the water from the inlet of the bed to the outlet. Also, broken beads can also cause channeling, which reduces the amount of water that the bed of beads can treat, thus making it necessary to regenerate the beads more often, which in turn increases chemical costs and increases the osmotic stress on the beads.

When the intended use of the resin is as a catalyst, the functionalized collection of polymeric beads, herein referred to as a "resin," is employed by bringing the resin into contact with one or more reactants and allowing a chemical reaction to take place involving the one or more reactants, to produce one or more products. In a preferred catalyst embodiment, the collection of polymeric beads is functionalized with sulfonic acid groups to produce an SAC. When used as a catalyst, the SAC is referred to as an "acid catalyst."

Resins that are intended for use as catalysts may be characterized by their moisture hold capacity (MHC). MHC is the amount of water present in a collection of polymeric beads when bulk liquid water has been separated from the beads and the beads have been allowed to come to equilibrium with air having 100% relative humidity. Preferably, the MHC of resins intended for use as catalysts is, by weight based on the total weight of the collection of resin beads, including the beads and the water, is 90% or less; more preferably 80% or less. Preferably, prior to contact with acetone and phenol, the amount of water present in the resin, by weight based on the weight of the resin, is 50% or more; more preferably 60% or more.

Preferred reactants are acetone and phenol, reacting to make 2,2-bis(4-hydroxyphenyl)propane (also called bisphenol A). It is contemplated that two moles of phenol react with one mole of acetone to make one mole of bisphenol A and one mole of water. In bisphenol A formation, preferred resin catalysts are SAC resins. Prior to contact with acetone and phenol, the resin may or may not be reacted with a promoter. In preferred embodiments, prior to contact with acetone and phenol, the resin is reacted with a promoter. Preferred promoters have both an amine group and a thiol group. Preferably, the amine groups on the promoter attach to sulfonic acid groups on the resin. Preferably, the mole percent of sulfonic acid groups attached to an amine group of a promoter is 5% to 50%. Preferably, prior to contact with acetone and phenol, the water is removed from the collection of resin beads, for example by rinsing with phenol. Preferably, immediately prior to contact with acetone and phenol, the water content in the collection of polymeric beads is, by weight based on the collection of polymeric beads, 2% or less; more preferably 1% or less.

Preferably, while the resin is in contact with the phenol and the acetone, the resin is at temperature of 55° C. or higher; more preferably 60° C. or higher.

When the intended use is catalysis, the resistance to crushing is also an advantage. The lifetime of resins of the present invention will be higher, and the reduced level of fine particles will enable reactants to pass through the bed of resin with lower pressure drop.

The following are examples of the present invention.

The following terms, abbreviations, and materials were used:

Jetted=monomer droplets were introduced into the aqueous medium using the jetting procedure described in U.S. Pat. Nos. 4,444,960 and 4,623,706 tBC=4-t-butylcatechol; some tBC is present in the grade of DVB that was used.

DVB=divinylbenzene, produced and supplied by the Dow Chemical Company. The grade of DVB that was used was a mixture that contained 63% pure divinylbenzene and approximately 37% ethylvinylbenzene by weight. The percentages of DVB listed below refer to the amount of pure DVB. When DVB is present, it is assumed that EVB is also present in a weight ratio of EVB:DVB of approximately 37:63. DVB contains approximately 1000 ppm by weight of tBC.

tBC-free DVB=DVB that contains no tBC. To make tBC-free DVB, the tBC was stripped from the portion of DVB indicated by a series of 4% NaOH batch washes.

CMMC=carboxymethyl methylcellulose, produced and supplied by The Dow Chemical Co.

PVOH=SELVOL™ 523 polyvinyl alcohol, from Sekisui Specialty Chemicals

HEMC=WALOCEL™ MKX 15000 PF 01 hydroxyethyl cellulose, from the Dow Chemical Company SBA=strong base anion exchange resin; copolymer of styrene/DVB functionalized with quaternary ammonium groups SAC=strong acid cation exchange resin; copolymer of styrene/DVB, functionalized sulfonic acid groups Tris=tris(hydroxymethyl)aminomethane, 100% solid supplied by Fisher Scientific, used as 20% by weight solution in water PADMAC=solution in water of 20% by weight poly(diallyldimethyl ammonium chloride), also called poly(DADMAC).

gelatin=animal based gelatin, isoelectric point approximately 8.5

VPBA=4-vinylphenyl boronic acid

BPO=benzoyl peroxide, 75% purity by weight

DI water=deionized water

Dichromate: =sodium dichromate dihydrate solution, concentration=70% dihydrate in water by weight GA=gradual addition ambient temperature=approximately 23° C.

Eight protocols for suspension polymerization were used, labeled A, B, D, E, F, G, and H. The protocols are distinguished by the parameters as follows. After copolymer beads were formed, they were functionalized using the method listed in the final column. The details of the functionalization methods are shown below the table.

| | polymer[1] | inhibitor[2] | formation[3] | total DVB[4] | functionalization |
|---|---|---|---|---|---|
| A | CMMC + PVOH | $NaNO_2$ | jetted | 4.65% | sulfonation |
| B | CMMC + PVOH | $NaNO_2$ | jetted | 5.2% | sulfonation |
| C | CMMC + PVOH | $NaNO_2$ | jetted | 4.65 to 5.2% | sulfonation |
| D | CMMC + PVOH | $NaNO_2$ | jetted | 2.0 to 2.8% | sulfonation |
| E | PADMAC + gelatin | $NaNO_2$ | jetted | 4.65% | sulfonation |
| F | CMMC + PVOH | $NaNO_2$ | jetted | 9.2 to 11.0% | sulfonation |
| G | HEMC | dichromate | agitation | 7.6 to 9.0% | sulfonation |
| H | PADMC + gelatin | $NaNO_2$ | jetted | 4.65% | CM/A |

[1]Water-soluble polymer in the aqueous medium

[2]Inhibitor in the aqueous medium

[3]Whether the droplets are formed by jetting or by agitation

[4]The total amount by weight percentage of DVB in the entire process, as a percentage of total monomer weight.

In preparation of the droplet mixtures or the aqueous media described below, some partial mixtures were sometimes heated above 25° C. to achieve good mixing. However, at the time when the droplets were formed and suspended in the aqueous medium, all the ingredients were at ambient temperature.

Where copolymers were converted to SAC resins, the copolymer-containing polymeric beads were sulfonated by standard sulfonation processes, using sulfuric acid, to achieve a degree of substitution such that at least 95 mole % of aromatic rings on polymerized units of monofunctional vinyl monomer, based on the total polymerized units of monofunctional vinyl monomer, had a sulfonate group.

Crush Strength was measured as follows. Functionalized polymeric beads were placed into contact with air at 100% humidity at 50° C. for 4 days. Then the beads were covered with deionized water and stored for one hour or more at room temperature (approximately 23° C.). A single bead was placed on one plate of a compression tester at room temperature, and the bead was covered with one drop of water. The plates are brought together at 6.0 mm/min until the particle fractures, and the peak force is noted. The procedure is repeated for at least 30 beads, and the average peak force is reported as the "crush strength." The test apparatus was a Chatillon™ force tester model TCD 200, with a medium-slow motor (2.5 to 63.5 mm/min). Force gauge was model DFGS10. Crush strength is reported in grams of force per bead (g/bd).

Osmotic stability (OS) was measured as follows. Functionalized polymeric beads were conditioned by contact with a solution of NaCl in water at ambient temperature (approximately 23° C.). The NaCl solution was decanted, and the wet resin was passed through mesh screens to produce a sample of resins having diameter of 500 μm to 710 μm. Then resin was placed in a vertical straight-walled glass column. A single cycle was as follows: fluid drained from the column by gravity; resin in the column was contacted with solution #1; the column was backwashed with water; fluid drained from the column by gravity; resin in the column was contacted with solution #2; the fluid was drained from the column, the column was backwashed with water. The test was repeated for 50 cycles. Solution #1 was $H_2SO_4$ in water. Solution #2 was NaOH in water. The cycles of exposure to different solutions causes some particles to break. After the cycles of exposure, the beads were placed on a screen that passes objects of diameter less than 500 μm. The material retained on the screen is considered to be whole beads, and the material passing through the screen is considered to be fragments of broken beads. The osmotic stability is $$OS(\%)=100\times W_{frag}/(W_{whole}+W_{frag})$$

where $W_{frag}$=weight of fragments, and $W_{whole}$=weight of whole beads. Lower OS values are more desirable.

Functionalized resin samples were tested for storage stability as follows. Resin was separated from bulk water and brought into equilibrium with air at ambient temperature and 100% relative humidity. Resin was then placed in a closed vial and stored for 30 days at ambient temperature. Then the resin was thoroughly mixed with DI water in a weight ratio of 3 parts water to 1 part resin. Water was removed by filtration, and the water was tested for conductivity and for absorbance at wavelength of 350 nm, using standard instruments.

In all protocols except G, the weight ratio of droplet ingredients to aqueous phase ingredients was 0.61:1. In protocol G, the weight ratio of droplet ingredients to aqueous phase ingredients was 1:1. When DVB was gradually added during polymerization, the addition was continuous over the extent range shown in the table in Example R1 below. DVB addition, while continuous, varied in rate during the course of the addition.

The compositions of the starting droplets (immediately prior to the initiation of polymerization) in the following examples were as follows. Amounts are % by weight based on the weight of the monomer droplets. (All samples with the same prefix used the same composition of aqueous medium. For example, all of examples A-2a(1), A-2a(2), and A-2b used the same aqueous medium composition, labeled "A-2"). Total weight of each monomer droplet composition was 100%. Samples with suffix "Comp" are used in comparative methods. BPO as initiator was present in all starting droplets.

| Example | DVB | Stabilizer Aid | t-BC-free DVB | Styrene |
|---|---|---|---|---|
| A-1Comp | 4.65 | VPBA | 0 | balance |
| A-2a | 2.0 | VPBA | 0 | balance |
| A-2b | 2.0 | VPBA | 0 | balance |
| A-2c | 0.8 | VPBA | 0 | balance |
| B-1Comp | 2.25 | none | 2.95 | balance |
| B-2 | 2.25 | none | 0 | balance |
| C-1Comp | 4.65 | none | 0 | balance |
| C-2 | 2.25 | none | 0 | balance |
| D-1Comp | 2.0 | VPBA | 0 | balance |
| D-2a | 0.8 | none | 0 | balance |
| D-2b | 1.1 | none | 0 | balance |

| Example | DVB | Stabilizer Aid | Styrene |
|---|---|---|---|
| E-1 | 4.65 | none | balance |
| E-2 | 2.0 | none | balance |
| F-1 | 9.2 | VPBA | balance |
| F-2 | 4.65 | none | balance |
| G-1 | 7.6 | none | balance |
| G-2 | 3.9 | none | balance |

The compositions of the aqueous media in the following examples were as follows. Amounts are % by weight based on the weight of the aqueous medium. In all cases, the aqueous phase concentration of stabilizers was such that the number percentage of beads having sphericity of 0.8 or higher was at least 99%, based on the total number of beads. In all cases, the aqueous or monomer phase concentration of stabilizer was such that the number percentage of having sphericity of 0.8 or higher was at least 99%, based on the total number of beads. In all cases, the aqueous phase concentration of latex inhibitor was such that the weight percentage of emulsion polymer at the end of the reaction was less than 0.5%, based on the total weight of polymeric beads.

The harmonic mean diameter of the final polymer beads formed by jetting was 430-470 micrometers. For droplets formed by agitation, the harmonic mean diameter of the final polymer beads was 490-650 micrometers.

| Example | Stabilizer | Latex Inhibitor | Stabilizer Aid |
|---|---|---|---|
| A-1Comp | CMMC + PVOH | $NaNO_2$ | none |
| A-2 | CMMC + PVOH | $NaNO_2$ | none |
| B-1 Comp | CMMC + PVOH | $NaNO_2$ | VPBA |
| B-2 | CMMC + PVOH | $NaNO_2$ | VPBA |
| C-1 Comp | CMMC + PVOH | $NaNO_2$ | VPBA |
| C-2 | CMMC + PVOH | $NaNO_2$ | VPBA |
| D-1 Comp | CMMC + PVOH | $NaNO_2$ | none |
| D-2 | CMMC + PVOH | $NaNO_2$ | VPBA |

| Example | Stabilizer | Latex Inhibitor |
|---|---|---|
| E-1Comp | Gelatin + PADMAC | $NaNO_2$ |
| E-2 | Gelatin + PADMAC | $NaNO_2$ |

| Example | Stabilizer | Latex Inhibitor | Stabilizer Aid |
|---|---|---|---|
| F-1Comp | CMMC + PVOH | $NaNO_2$ | none |
| F-2 | CMMC + PVOH | $NaNO_2$ | VPBA |
| G-1Comp | HEMC | Dichromate | none |
| G-2 | HEMC | Dichromate | none |

COMPARATIVE EXAMPLE A1-COMP (NO ADDITION OF MONOMER AFTER INITIATION OF POLYMERIZATION), USING PROTOCOL A

Aqueous suspension polymerization was conducted on the reaction mixture as follows. A combination of reaction temperature and BPO concentration was chosen to result in an extent of conversion of 80-85% within 330-390 minutes. Once conversion to polymer was in the 80-85% range, pH was adjusted by Tris addition to the reactor—such that the final pH was in the 8-9 range. The reaction system was heated to 97° C. After 1 hour at 97° C., the system was cooled to ambient temperature and the beads were dewatered, washed with water, and dried at ambient temperature. Two identical polymerizations were conducted.

EXAMPLE A-2A AND A-2B, ALSO USING PROTOCOL A

Aqueous suspension polymerization was conducted on the reaction mixture as follows. A combination of reaction temperature and BPO concentration was chosen to result in an extent of conversion of 80-85% within 390-550 minutes. Once reaction temperature was reached, DVB was fed to the reactor, over the extent range shown in the table in Example R1 below, with the DVB feed rate varying with time. Two duplicate polymerizations of A-2a were performed, labeled A-2a(1) and A-2a(2).

Once conversion to polymer was in the 60-75% range, Tris was added to the reactor, such that the final pH was in the range of 8-9. The reaction system was heated to 97° C. within 60 minutes of Tris addition. After 1 hour, the system was cooled to ambient temperature and the beads were dewatered, washed with water and dried at ambient temperature.

EXAMPLE A-2C, ALSO USING PROTOCOL A

Aqueous suspension polymerization was conducted on the reaction mixture as follows. A combination of reaction temperature and BPO concentration was chosen to result in an extent of conversion of 80-85% within 390-550 minutes Once reaction temperature was reached, DVB was fed to the reactor, over the extent range shown in the table in Example R1 below, with the DVB feed rate varying with time.

Once conversion to polymer was in the 60-75% range, Tris was added to the reactor, such that the final pH was in the 8-9 range. The reaction system was heated to 97° C. within 60 minutes of the Tris addition. After 1 hour, the system was cooled to ambient temperature and the beads were dewatered, washed with water and dried at ambient temperature.

COMPARATIVE EXAMPLE B1-COMP (NO ADDITION OF MONOMER AFTER INITIATION OF POLYMERIZATION), USING PROTOCOL B

Aqueous suspension polymerization was conducted on the reaction mixture as follows. A combination of reaction temperature and BPO concentration was chosen to result in an extent of conversion of 80-85% within 480-560 minutes. Once at reaction temperature, a feed of 0.1% tBC in water to the reactor was started. The tBC feed rate varied with time, to simulate the tBC feed that would normally accompany a DVB feed.

tBC was gradually added from Extent 0% to 57%. Prior to initiation of polymerization, tBC concentration in the monomer droplets was 0.0055% by weight. At the end of the tBC feed, the tBC concentration in the monomer droplets (partially or fully converted to polymer) was 0.0101% by weight.

Once conversion to polymer was in the 80-85% range, pH was adjusted by Tris addition to the reactor, such that the final pH was in the range of 8-9. The reaction system was heated to 97° C. After 1 hour, the system was cooled to ambient temperature and the beads were dewatered, washed with water, and dried at ambient temperature.

EXAMPLES B-2A, B-2B, B-2C, B-2D, B-2E, AND B-2F, ALSO USING PROTOCOL B

Duplicate samples of B-2b were made, labeled B-2b(1) and B-2b(2).

Aqueous suspension polymerization was conducted on the reaction mixture as follows. A combination of reaction temperature and BPO concentration is chosen to result in an extent of conversion of 80-85% within 420-600 minutes. Once reaction temperature was reached, DVB was fed to the reactor, over the extent range shown in the table in Example R1 below, with the DVB feed rate varying with time.

Once conversion to polymer was in the 60-85% range, Tris was added to the reactor, such that the final pH was in the 8-9 range. The reaction system was heated to 97° C. within 60 minutes of the Tris addition. After 1 hour, the system was cooled to ambient temperature and the beads were dewatered, washed with water and dried at ambient temperature.

COMPARATIVE EXAMPLE C1-COMP (NO ADDITION OF MONOMER AFTER INITIATION OF POLYMERIZATION), USING PROTOCOL C

Aqueous suspension polymerization was conducted on the reaction mixture as follows. A combination of reaction temperature and BPO concentration is chosen to result in an extent of conversion of 80-85% within 330-390 minutes. Once reaction temperature was reached, Tris was added to the reactor such that the final aqueous pH was in the 8-9 range. Once conversion was in the 80-85% range, the system was heated to 97 C. After 1 hour at 97° C., the system was cooled to ambient temperature and the beads were dewatered, washed with water, and dried at ambient temperature.

EXAMPLE C-2, USING PROTOCOL C

Aqueous suspension polymerization was conducted on the reaction mixture as follows. A combination of reaction temperature and BPO concentration is chosen to result in an extent of conversion of 80-85% within 420-600 minutes. Once reaction temperature was reached, DVB was fed to the reactor, over the extent range shown in the table in Example R1 below, with the DVB feed rate varying with time.

Once conversion was in the 60-85% range, Tris was added to the reactor such that the final pH was in the 8-9 range. The reaction system was heated to 97° C. within 60 minutes of the Tris addition. After 1 hour, the system was cooled to ambient temperature and the beads were dewatered, washed with water and dried at ambient temperature.

COMPARATIVE EXAMPLE D1-COMP (NO ADDITION OF MONOMER AFTER INITIATION OF POLYMERIZATION), USING PROTOCOL D

Aqueous suspension polymerization was conducted on the reaction mixture as follows. A combination of reaction temperature and BPO concentration is chosen to result in an extent of conversion of 80-85% within 420-600 minutes. Once conversion to polymer was in the 80-85% range, pH was adjusted by Tris addition to the reactor—such that the final pH is in the 8-9 range. The reaction system was heated to 97° C. After 1 hour, the system was cooled to ambient temperature and the beads were dewatered, washed with water, and dried at ambient temperature. Two identical polymerizations were conducted.

EXAMPLE D-2A, USING PROTOCOL D

Aqueous suspension polymerization was conducted on the reaction mixture as follows. A combination of reaction temperature and BPO concentration is chosen to result in an extent of conversion of 80-85% within 390-550 minutes. Once reaction temperature was reached, DVB was fed to the reactor, over the extent range shown in the table in Example R1 below, with the DVB feed rate varying with time. Two duplicate polymerizations, labeled D-2a(1) and D-2a(2), were performed.

Once conversion to polymer was in the 20-30% range, Tris buffer was added to the reactor, such that the final pH was in the 8-9 range. Additional Tris buffer was added when conversion reached 80-85% such that the final pH was in the range of 8-9. The reaction system was then heated to 97° C. within 60 minutes of the Tris addition. After 1 hour, the system was cooled to ambient temperature and the beads were dewatered, washed with water and dried at ambient temperature.

EXAMPLE D-2B, USING PROTOCOL D

The same protocol as in D-2a was used, except that DVB was gradually added over the extent range shown in the table in Example R1 below. Two duplicate polymerizations, labeled D 2b(1) and D-2b(2), were performed.

COMPARATIVE EXAMPLE E-1COMP (NO ADDITION OF MONOMER AFTER INITIATION OF POLYMERIZATION), USING PROTOCOL E

Aqueous suspension polymerization was conducted on the reaction mixture as follows. A combination of reaction temperature and BPO concentration is chosen to result in an extent of conversion of 80-85% within 210-270 minutes. Once conversion to polymer was in the 80-85% range, the reaction system was heated to 92° C. After 1 hour, the system was cooled to ambient temperature and the beads were dewatered, washed with water, and dried at ambient temperature.

EXAMPLE E-2, USING PROTOCOL E

Aqueous suspension polymerization was conducted on the reaction mixture as follows. A combination of reaction temperature and BPO concentration is chosen to result in an extent of conversion of 80-85% within 300-360 minutes. Once reaction temperature was reached, DVB was fed to the reactor, over the extent range shown in the table in Example R1 below, with the DVB feed rate varying with time.

Once conversion to polymer was in the 80-85% range, the reaction system was heated to 92° C. After 1 hour, the system was cooled to ambient temperature and the beads were dewatered, washed with water and dried at ambient temperature.

COMPARATIVE EXAMPLE F1-COMP (NO ADDITION OF MONOMER AFTER INITIATION OF POLYMERIZATION), USING PROTOCOL F

Aqueous suspension polymerization was conducted on the reaction mixture as follows. A combination of reaction temperature and BPO concentration is chosen to result in an extent of conversion of 80-85% within 300-360 minutes. Once conversion to polymer was in the 80-85% range, pH was adjusted by Tris addition to the reactor—such that the final pH is in the 8-9 range. The reaction system was heated to 97° C. After 1 hour, the system was cooled to ambient temperature and the beads were dewatered, washed with water, and dried at ambient temperature.

EXAMPLE F-2, USING PROTOCOL F

Aqueous suspension polymerization was conducted on the reaction mixture as follows. A combination of reaction temperature and BPO concentration is chosen to result in an extent of conversion of 80-85% within 330-390 minutes. Once reaction temperature was reached, tBC-free DVB was fed to the reactor, over the extent range shown in the table in Example R1 below, with the DVB feed rate varying with time.

Once conversion to polymer was in the 80-85% range, Tris was added to the reactor, such that the final pH was in the 8-9 range. The reaction system was heated to 97° C. within 60 minutes of the Tris addition. After 1 hour, the system was cooled to ambient temperature and the beads were dewatered, washed with water and dried at ambient temperature.

COMPARATIVE EXAMPLE G1-COMP (NO ADDITION OF MONOMER AFTER INITIATION OF POLYMERIZATION), USING PROTOCOL G

Aqueous suspension polymerization was conducted on the reaction mixture as follows. A combination of reaction temperature and BPO concentration is chosen to result in an extent of conversion of 80-85% within 300-360 minutes. Once conversion to polymer was in the 80-85% range, the reaction system was heated to 90 C. After 3 hours, the system was cooled to ambient temperature and the beads were dewatered, washed with water and dried at ambient temperature.

EXAMPLE G-2, USING PROTOCOL G

Aqueous suspension polymerization was conducted on the reaction mixture as follows. A combination of reaction temperature and BPO concentration was chosen to result in an extent of conversion of 80-85% within 420-600 minutes. Once reaction temperature was reached, DVB was fed to the reactor, over the extent range shown in the table in Example R1 below, with the DVB feed rate varying with time.

Once conversion to polymer was in the 80-85% range, the reaction system was heated to 90 C. After 3 hours, the system was cooled to ambient temperature and the beads were dewatered, washed with water and dried at ambient temperature.

EXAMPLE R1: RESULTS OF PHYSICAL STABILITY TESTING SAC RESINS

Copolymers made with the above protocols were converted to SAC resins and tested as described above. Results were as follows. Where duplicate samples were tested, the average results are shown.

method=refers to whether the polymerization method had the gradual addition (GA) step of the present invention or not.

init DVB=the amount of DVB in the monomer droplets prior to initiation of polymerization, (by weight based on the weight of the monomer droplets)

final DVB=the amount of polymerized units of DVB in the finished polymer, by weight based on the total weight of all monomer used in the entire process, including the initial droplets and the DVB fed during polymerization EXTSTART=extent of reaction at which DVB feed was begun EXTSTOP=extent of reaction at which DVB feed was ended DIAM=harmonic mean diameter of polymeric beads

| Example | method | init DVB (%) | final DVB (%) | EXT-START (%) | EXT-STOP (%) | DIAM (μm) | Crush (g/bd) | OS (%) |
|---|---|---|---|---|---|---|---|---|
| A-1 Comp | no GA | 4.65 | 4.65 | none | none | 450 | 806 | 12.4 |
| A-2a | GA | 2 | 4.65 | 0 | 60 | 450 | 3242 | 1.8 |
| A-2b | GA | 2 | 4.65 | 0 | 85 | 450 | 2882 | 2.7 |
| A-2c | GA | 0.8 | 4.65 | 0 | 58 | 450 | 2458 | 1.1 |
| B-1 Comp | no GA | 5.2 | 5.2 | none | none | 450 | 1375 | 1.7 |
| B-2a | GA | 2.25 | 5.2 | 0 | 78 | 450 | 3271 | 1.6 |
| B-2b | GA | 2.25 | 5.2 | 0 | 59 | 450 | 3649 | 1.2 |
| B-2c | GA | 2.25 | 5.2 | 0 | 24 | 450 | 3736 | 0.6 |
| B-2d | GA | 2.25 | 5.2 | 0 | 5 | 450 | 4215 | 0.4 |
| B-2e | GA | 2.25 | 5.2 | 15 | 43 | 450 | 2700 | 0.4 |
| B-2f | GA | 2.25 | 5.2 | 27 | 33 | 450 | 2673 | 0.7 |
| C-1 Comp | no GA | 4.65 | 4.65 | none | none | 450 | 838 | 13.8 |
| C-2 | GA | 2.25 | 5.2 | 0 | 62 | 450 | 2646 | 2.7 |
| D-1 Comp | no GA | 2.0 | 2.0 | none | none | 450 | 916 | 11.1 |
| D-2a | GA | 0.8 | 2.0 | 0 | 74 or 75 | 450 | 1470 | 2.3 |
| D-2b | GA | 1.1 | 2.8 | 0 | 80 or 85 | 450 | 1773 | 2.0 |
| E-1 Comp | no GA | 4.65 | 4.65 | none | none | 460 | 830 | 17.2 |
| E-2 | GA | 2.0 | 4.65 | 0 | 80 | 460 | 1044 | 3.9 |
| F-1 Comp | no GA | 9.2 | 9.2 | none | none | 450 | 2125 | 0.4 |
| F-2 | GA | 4.65 | 11.0 | 0 | 67% | 450 | 3412 | 0.1 |
| G-1 Comp | no GA | 7.6 | 7.6 | none | none | 450 | 560 | 8.6 |
| G-2 | GA | | | | | 450 | 2420 | 1.4 |

EXAMPLE R2: RESULTS OF TESTING OF SAMPLES OF PROTOCOL E

From the copolymers of protocol E, Strong Base Anion (SBA) exchange resins were made by a standard process of chloromethylation using chloromethyl ether followed by amination using trimethyl amine, such that at least 95 mole % of aromatic rings on polymerized units of monofunctional vinyl monomer, based on the total polymerized units of monofunctional vinyl monomer, had an amine-containing group attached.

The SBA resins were tested as in Example A-R. Results were as follows:

| Example | method | init DVB (%) | final DVB (%) | EXT-START (%) | EXT-STOP (%) | DIAM (μm) | Crush (g/bd) | OS (%) |
|---|---|---|---|---|---|---|---|---|
| H-1Comp | no GA | 4.65 | 4.65 | none | none | 450 | 160 | 53.8 |
| H2 | GA | 2.0 | 4.65 | 0 | 80% | 450 | 324 | 37.0 |

EXAMPLE R3: RESULTS OF CATALYSIS

Various functionalized resin samples were tested for activity in catalyzing the reaction between phenol and acetone to make bisphenol-A (BPA). The catalytic activity is characterized by the time to 60% conversion ("T60%"). Shorter times reflect higher level of catalytic activity.

The catalysis reactions were carried out as follows: Resin was rinsed with phenol to remove moisture from the beads. Phenol was added to a glass reactor and heated at 50° C. to melt the phenol. Dry resin, loaded with promoter, was added to the reactor and allowed to swell in the phenol. Reactor temperature was regulated at a temperature between 45° C. and 80° C. Acetone was added to the reactor. At time intervals, a small sample of the liquid in the reactor was removed by pipette, placed in a vial, and mixed with excess N-Methyl-N-(trimethylsilyl) trifluoroacetamide. Vials were stored for 30 minutes at 60° C., then cooled to ambient temperature, then tested by Gas Chromatography for BPA content.

The catalysis results were as follows. All of the samples shown had total amount of polymerized units of DVB of 4.65%.

| Example | A-2a | A-2b | A-2c | C-1Comp |
| --- | --- | --- | --- | --- |
| T60% (min) | 52 | 52 | 47 | 71 |

Samples A-2a, A-2b, and A-2c, which were made using gradual addition according to the present invention, had much shorter times to 60% conversion than the comparative sample.

EXAMPLE R4: RESULTS OF STORAGE FOR 30 DAYS AT AMBIENT TEMPERATURE

Storage results were as follows:

| Example: | A-1Comp | A-2a | A-2b | C-1Comp | C-2 |
| --- | --- | --- | --- | --- | --- |
| Conductivity (μS) | 169 | 127 | 160 | 189 | 126 |
| Absorbance | 0.225 | 0.165 | 0.171 | 0.235 | 0.137 |

Each Example resin showed lower conductivity and absorbance than its corresponding comparative example. That is, samples A-2a and A-2b showed lower conductivity and absorbance than comparative A-1Comp. Similarly, sample C-2 showed lower conductivity and absorbance than comparative C-1Comp. This result shows that the Example resins have greater stability during storage.

The invention claimed is:

1. A process for producing 2,2-bis(4-hydroxyphenyl)propane, comprising condensing phenol with acetone in the presence of an acid catalyst to produce dihydric phenol 2,2-bis(4-hydroxyphenyl) propane;

wherein the acid catalyst comprises a collection of sulfonated polymeric beads, wherein the sulfonated polymeric beads comprise (i) 75 to 99% by weight, based on the weight of the bead, polymerized units of monofunctional vinyl monomer, and (ii) 1 to 25% by weight, based on the weight of the bead, polymerized units of multifunctional vinyl monomer;

wherein, within each bead, the average concentration of moles of polymerized units of multifunctional vinyl monomer per cubic micrometer is MVAV; and wherein, within each bead, T1000 is a sequence of 1,000 unique connected polymerized monomer units;

wherein, within each T1000, MVSEQ is the weight percent polymerized units of multifunctional vinyl monomer, based on the weight of T1000;

wherein MVRATIO=MVSEQ/MVAV;

and wherein 90% or more of the beads by volume are uniform beads, wherein a uniform bead is a bead in which 90% or more of all T1000 sequences has MVRATIO of 1.5 or less.

2. The process of claim 1, wherein the acid catalyst additionally comprises a thiol compound.

3. The process of claim 1, wherein the condensation is conducted at 55° C. or above.

4. The process of claim 1, wherein 35% or less of the T1000 sequences have MVRATIO of 0.5 or less.

* * * * *